United States Patent [19]

Krall et al.

[11] 4,225,510
[45] Sep. 30, 1980

[54] PREPARATION OF PERCHLORO-2,5-DIAZA-1,5-HEXADIENE

[75] Inventors: Hermann D. Krall, Meerbusch; Herbert Schwarz, Leverkusen, both of Fed. Rep. of Germany

[73] Assignee: Bayer Aktiengesellschaft, Leverkusen, Fed. Rep. of Germany

[21] Appl. No.: 974,413

[22] Filed: Dec. 29, 1978

[30] Foreign Application Priority Data

Jan. 25, 1978 [DE] Fed. Rep. of Germany ....... 2803124

[51] Int. Cl.$^2$ ............................................. C07C 119/00
[52] U.S. Cl. ............................ 260/566 D; 260/566 R
[58] Field of Search ..................... 260/566 R, 566 D

[56] References Cited

U.S. PATENT DOCUMENTS

| | | | |
|---|---|---|---|
| 3,206,516 | 9/1965 | Ziegenbein et al. | 260/566 D |
| 3,251,760 | 5/1966 | Holtschmidt et al. | 260/566 D |
| 3,267,144 | 8/1966 | Ottmann et al. | 260/566 D |
| 3,301,893 | 1/1967 | Degener et al. | 260/566 D |

OTHER PUBLICATIONS

Beck, von Gunther et al. Angew. Chem., vol. 86, p. 134 (1974).

*Primary Examiner*—Natalie Trousof
*Assistant Examiner*—L. Hendriksen
*Attorney, Agent, or Firm*—Sprung, Felfe, Horn, Lynch & Kramer

[57] ABSTRACT

In the preparation of perchloro-2,5-diaza-1,5-hexadiene by chlorination of N,N-dimethylaminoacetonitrile, the improvement which comprises in a first stage (a) chlorinating N,N-dimethylaminoacetonitrile or its hydrochloride at about 70° to 80° C. in a solvent, removing the solvent by distillation under chlorinating conditions until a bottom temperature of about 120° to 160° is reached, and after-treating the residual reaction at this temperature with chlorine, and in a second stage (b) chlorinating the resulting reaction mixture at a temperature from about 150° to 220° C. Advantageously the solvent in stage (a) is phosphorus oxychloride, the weight ratio of nitrile to solvent is about 1:3, the after-chlorination in stage (a) is carried out at a temperature from about 120° to 140° C., and stage (b) is carried out at a temperature from about 180° to 210° C. in a multistage bubble column cascade reactor operated with gas and liquid in counter-current.

8 Claims, No Drawings

PREPARATION OF PERCHLORO-2,5-DIAZA-1,5-HEXADIENE

The present invention relates to an unobvious process for the preparation of the known compound perchloro-2,5-diaza-1,5-hexadiene (which can be used as an intermediate product for the synthesis of pesticidal active compounds) by the chlorination of N,N-dimethylaminoacetonitrile.

The chlorination of N,N-dimethylaminoacetonitrile is mentioned in the literature (for example in DT-AS (German Published Specification) No. 1,221,212) and proceeds via chlorinated N-methyl-imidazoles and -imidazolines (see also Angew. Chem. 86, 134 (1974)). However, no precise data on the reaction conditions and the yield are given. If, now, practical experiments are carried out to synthesize perchloro-2,5-diaza-1,5-hexadiene in accordance with the instructions in the literature, by dissolving N,N-dimethylaminoacetonitrile in 1,2,4-trichlorobenzene and first chlorinating at a temperature of 70° to 80° C. until the very highly exothermic reaction has ended, then continuing the chlorination while increasing the temperature by 10° to 15° C. per hour and finally chlorinating further for three hours more at 200° to 230° C., it is found that only an unsatisfactory amount of perchloro-2,5-diaza-1,5-hexadiene has formed, and the amount of the latter in the reaction product cannot be further increased even on further treatment with chlorine.

Economic use of the reaction is not possible under these conditions.

It has now been found that the known compound perchloro-2,5-diaza-hexadiene can be obtained in good yield and purity by chlorination of N,N-dimethylaminoacetonitrile when, with precise temperature control (a) in a first stage the chlorination of N,N-dimethylaminoacetonitrile or the hydrochloride thereof is carried out at about 70° to 80° C., in a solvent, the solvent is then removed by distillation under chlorinating conditions until a bottom temperature of about 120° to 160° C. is reached and the residual reaction mixture is after-treated at this temperature with chlorine and (b) in a second stage, the resulting reaction mixture is subjected to high-temperature chlorination at temperatures up to 220° C.

It is extremely surprising that with the two-stage procedure according to the invention perchloro-2,5-diaza-1,5-hexadiene can be obtained in yields of more than 90% and in a degree of purity of more than 99%, while the yields according to the process known from the literature are considerably lower. The process according to the invention thus represents an enrichment of the art.

Overall, the chlorination reaction which starts from N,N-dimethylaminoacetonitrile proceeds in accordance with the following reaction equation, the chlorinated N-methylimidazoles and N-methyl-imidazolines formed as intermediates being disregarded:

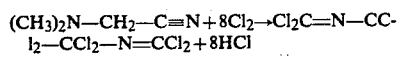

N,N-Dimethylaminoacetonitrile, which is used as the starting material, is a compound which has been known for a long time (see, for example, J. Am. Chem. Soc. 68, 1,607 (1946) and Liebigs Ann. Chem. 279, 43 (1894)). It is prepared by a "Mannich reaction" from dimethylamine, formaldehyde and hydrocyanic acid.

The process according to the invention is clearly divided into two stages. The reaction is carried out in the presence of diluents in the first stage and in the absence of diluents in the second stage.

Diluents which can be used in the first stage of the process according to the invention are inorganic acid halides, such as, for example, thionyl chloride or sulphuryl chloride. The use of phosphorus oxychloride is preferred, however, because this results in the reaction mixture having an elevated boiling point and thus facilitates the condensation, in a reflux condenser, of amounts of liquid entrained in the stream of gas.

The quantitative ratio of N,N-dimethylaminoacetonitrile to solvent can be in the range of about 1:1 to 1:10 and a ratio of nitrile to solvent of about 1:3 is preferred.

The first stage of the process according to the invention is explained in more detail below:

The apparatus used to carry out the first stage of the process is generally a reactor such as is generally used for gas/liquid reactions, for example a container which can be heated and cooled and has a gas feed device and is fitted with a distillation column with a column head which during the subsequent removal of the solvent by distillation is operated, as desired, with an infinite reflux ratio (reflux condenser during the reaction) or with a finite reflux ratio.

The procedure employed in this stage depends on the starting material for the first stage (whether the N,N-dimethylaminoacetonitrile or the hydrochloride thereof). If the hydrochloride of N,N-dimethylaminoacetonitrile is chosen as the starting material, the suitable amounts of N,N-dimethylaminoacetonitrile and solvent are introduced into the chlorination apparatus described above, the amount of hydrogen chloride stoichiometrically required is passed into this mixture, whereupon the mixture warms to about 70° to 80° C., and the chlorination of the resulting suspension is started at this temperature. After chlorinating for about 15 hours at the indicated temperature, which is kept constant by cooling, the reaction mixture has become homogeneous. Analysis shows the presence of N-methyl-1-2,4,5-trichloroimidazole as the main component, in the reaction mixture, which does not form an insoluble hydrochloride in the solvent. By raising the temperature, the solvent is now distilled off in a stream of chlorine, in vacuo if appropriate, and the temperature in the kettle at the end of the distillation should not fall below about 110° C. and not rise above about 150° C.; preferably, the temperature should be from about 120° to 140° C.

Particularly preferably, the distillation is carried out at a maximum temperature of about 130° C. After the distillation has ended, the chlorination is continued at the temperatures mentioned above for the distillation for a further 5 to 10 hours until the reaction mixture essentially consists of chlorinated N-methyl-perchloro-2-imidazolines; if the reaction mixture is not further processed immediately, dissolved chlorine is then blown out with nitrogen and the mixture is cooled under nitrogen.

If N,N-dimethylaminoacetonitrile itself is used as the starting point for the chlorination, it is advisable initially to introduce half of the solvent used into an apparatus of the type described above and to pass chlorine into this solvent. N,N-Dimethylaminoacetonitrile is dissolved in the other half of the solvent and fed, in this mixture, into the reactor at a rate such that a reaction temperature of about 75° C. can be maintained with cooling. This measure is necessary in order to control the heats of reaction, because with this process variant the reaction enthalpy of the chlorination and that which results from the formation of the corresponding hydrochlorides from N,N-dimethylaminoacetonitrile, or its partially chlorinated derivatives, and the hydrogen chloride liberated during the chlorination are additive. The further course of reaction then corresponds to that explained above.

The second stage of the process according to the invention is explained in more detail below:

The reaction product obtained in the first stage of the process is subjected to a high-temperature chlorination in the second stage. In this stage, the chlorination temperatures are generally in the range from about 150° C. to 220° C., preferably about 160° to 210° C. and especially about 180° C. to 210° C.

The high-temperature chlorination can be carried out in the apparatuses known for chlorination, for example in a reaction kettle of the type which can already be used in the first stage of the process according to the invention. However, it is preferably carried out in apparatuses which ensure a better mass transfer between gas (chlorine) and liquid (reaction product from the first stage of the process), for example in a bubble column, which can operate discontinuously or continuously. A bubble column of this type can be constructed as a single-stage column but is preferably constructed as a multi-stage column, in the form of a bubble column cascade, and the reactants can be fed to one another in co-current, but preferably in counter-current.

The operation proceeds in the same way, independently of the apparatus used. The reaction mixture from the first stage of the process is fed into the apparatus used and reacted with chlorine at temperatures in the range of about 150° to 220° C. The reaction has ended after 8 to 15 hours and the reaction product—molten perchloro-2,5-diaza-1,5-hexadiene—is discharged from the reactor via a suitable device, for example a crystallizing screw. Another possibility for obtaining the product comprises, for example, taking up the hot reaction melt in a solvent in which the solubility of perchloro-2,5-diaza-1,5-hexadiene is low, for example carbon tetrachloride, chlorobenzene, 1,2-dichlorobenzene or the like, and then filtering off the products. A purifying effect is additionally achieved in this way and perchloro-2,5-diaza-1,5-hexadiene is obtained in the form of a mass of white crystals with a melting point of 167° C. (literature 166° C.).

Details of the course of reaction are explained in the preparative examples.

Perchloro-2,5-diaza-1,5-hexadiene, which is obtainable by the process according to the invention, is a known compound (compare, for example, DT-AS (German Published Specification) No. 1,221,212).

With hydrogen fluoride it gives N,N'-bis-(trifluoromethyl)-tetrafluoroethylenediamine, and perfluoro-2,5-diaza-hexa-2,4-diene is then obtained from the latter with sodium fluoride, with the elimination of 2 mols of hydrogen fluoride (in this connection see DT-AS (German Published Specification) No. 2,013,433 and U.S. Pat. No. 3,694,507; the compound is obtained by a different route as described by P. H. Ogden and R. A. Mitsch, J. Am. Chem. Soc. 89, 5,008 (1967)). With N-methyl-N'-(4-chlorophenyl)-thiourea, this perfluoro compound gives, in a cyclization reaction, 2-methylimino-3-(4'-chlorophenyl)-4,5-bis-(trifluoromethylimino-thiazolidine, which is a plant protection fungicide known from the literature (see DT-OS (German Offenlegungsschrift) No. 2,062,348 and U.S. Pat. No. 3,895,020).

PREPARATIVE EXAMPLES—FIRST STAGE/LOW-TEMPERATURE CHLORINATION

EXAMPLE 1

120 kg of phosphorus oxychloride were initially introduced into a 270 liter enamel kettle with oil circulation heating, provided with a distillation column with a column head, which could be operated with a finite or infinite reflux ratio as desired, and warmed to 70° C. and a stream of chlorine was passed in at this temperature. At the same time, the addition of a mixture of 60 kg of N,N-dimethylaminoacetonitrile and 120 kg of phosphorus oxychloride was started, the two components being pumped separately into a receiver, which then served as a dropping funnel. During this addition, the highly exothermic reaction started and this proceeded at about 75° C. After the addition of nitrile had ended, chlorination was continued for about a further 11 hours until the slightly brown-red reaction solution had become homogeneous. The removal of phosphorus oxychloride by distillation in a stream of chlorine at normal pressure was now started, the temperature being increased slowly and a bottom temperature of 130° C. not being exceeded.

After the distillation had ended, the reaction mixture was chlorinated for a further 10 hours at 130° C. and cooled under nitrogen.

This gave about 215 kg of a product mixture of the following composition:

|  | % by weight |
|---|---|
| phosphorus oxychloride | 3.2 |
| N-methyl-2,4,5-trichloroimidazole | 1.0 |
| N-methyl-perchloro-2-imidazoline | 1.5 |
| N-chloromethyl-perchloro-2-imidazoline | 88.2 |
| N-dichloromethyl-perchloro-2-imidazoline | 6.1 |
|  | 100.0 |

The yield of chlorinated imidazoles was 98.2% of theory, based on N,N-dimethylaminoacetonitrile employed.

EXAMPLE 2

A mixture of 235 kg of phosphorus oxychloride and 45 kg of N,N-dimethylaminoacetonitrile was initially introduced into a 270 liter enamel kettle with oil circulation heating, provided with a distillation column with a column head, which could be operated with an infinite or finite reflux ratio as desired, and the hydrochloride of the nitrile was prepared by passing in 19.5 kg of hydrogen chloride. During this reaction the temperature rose to about 75° C. Chlorine was then passed in for about 12 hours until the heterogeneous reaction solution had become homogeneous. The phosphorus oxychloride was now distilled off in a stream of chlorine, the temperature being increased slowly, but a bottom temperature of 130° C. not being exceeded. After the distillation had ended, the reaction mixture was chlorinated for a further 10 hours at 130° C. After cooling, this gave about 155 kg of a product of the following composition:

| | % by weight |
|---|---|
| phosphorus oxychloride | 4.3 |
| N-methyl-perchloro-2-imidazoline | 16.0 |
| 1,1,3,4,6-pentachloro-2,5-diaza-2,4-hexadiene | 0.3 |
| N-chloromethyl-2,4,5-trichloroimidazole | 0.7 |
| N-chloromethyl-perchloro-2-imidazoline | 78.2 |
| N-dichloromethyl-perchloro-2-imidazoline | 0.5 |
| | 100.0 |

The yield of chlorinated imidazoles was 97.6% of theory, based on N,N-dimethylaminoacetonitrile employed.

SECOND STAGE/HIGH-TEMPERATURE CHLORINATION

Description of the reactor:

The apparatus used in the examples which follow consisted of an eight-stage counter-current bubble column cascade reactor (1) which had a nominal diameter of 100 mm and a height of 300 mm per stage and which was made of glass. Sieve trays (3) were located between the individual segments (2) and pipe bends (4) fitted on the outside of the reactor served as the overflow, each pipe bend connecting two segments with one another (height of the overflow: 215 mm). The product from the first stage of the process (5) was pumped in at the top of this reactor and chlorine (6) flowed in counter-current thereto. The reaction product (7) was removed from the bottom of the bubble column and the hydrogen chloride (8) formed during the chlorination was absorbed in water (10) with the formation of hydrochloric acid (9). Each of these eight segments was provided with resistance heating (11), so that the process could be run with any desired temperature profile along the length of the reactor.

EXAMPLE 3

Per hour, 1,050 ml of a product mixture prepared according to Example 2 were introduced into the reactor described above and reacted with chlorine. The process was operated with a residence time of nine hours and the following temperature profile along the length of the reactor:

| stage 1 (top) | 130° C. |
|---|---|
| stage 2 | 180° C. |
| stage 3 | 180° C. |
| stage 4 | 190° C. |
| stage 5 | 190° C. |
| stage 6 | 200° C. |
| stage 7 | 200° C. |
| stage 8 | 210° C. |

In the steady state, 54.1 kg of perchloro-2,5-diaza-1,5-hexadiene with a purity of more than 99% were obtained from 45.3 kg of a product mixture which had been obtained, according to Example 2, from 13.6 kg of N,N-dimethylaminoacetonitrile. This corresponded to a yield of 95% in the second stage and a total yield of 93% over both stages of the process, based on N,N-dimethylaminoacetonitrile. A mixture was removed from the reactor with the stream of gas and, after condensing, this mixture gave 700 ml of a liquid which consisted of phosphorus oxychloride and N-methyl-perchloro-2-imidazoline and could be used again in other experiments.

EXAMPLE 4

Per hour, 720 ml of a product mixture prepared according to Example 1 were introduced into the bubble column described above and subjected to high-temperature chlorination.

With an average residence time of 13 hours, the individual stages of the reactor had the following temperatures:

| stage 1 (top) | 130° C. |
|---|---|
| stage 2 | 150° C. |
| stage 3 | 170° C. |
| stage 4 | 170° C. |
| stage 5 | 180° C. |
| stage 6 | 190° C. |
| stage 7 | 190° C. |
| stage 8 | 200° C. |

The reaction product contained 93.5% of perchloro-2,5-diaza-1,5-hexadiene in addition to 3% of N-dichloro-methyl-perchloro-2-imidazoline, 2.7% of N-dichloromethyl-2,4,5-trichloroimidazole, 0.2% of tetrachloropyrimidine, 0.1% of 1,1,3,3,3-pentachloro-2-aza-1-propene and 0.5% of unknown compounds.

EXAMPLE 5

Example 4 was repeated with the following temperature profile along the length of the reactor:

| stage 1 (top) | 130° C. |
|---|---|
| stage 2 | 150° C. |
| stage 3 | 170° C. |
| stage 4 | 180° C. |
| stage 5 | 180° C. |
| stage 6 | 190° C. |
| stage 7 | 200° C. |
| stage 8 | 200° C. |

The perchloro-2,5-diaza-1,5-hexadiene content in the product was 98.5%. The remainder consisted of N-dichloromethyl-2,4,5-trichloroimidazole.

EXAMPLE 6

900 ml/hour of a product obtained according to Example 1 were introduced into the reactor. With a total residence time of 10.5 hours and the indicated temperature profile, the reaction product indicated below was obtained:

| Temperature profile: | |
|---|---|
| stage 1 (top) | 130° C. |
| stage 2 | 170° C. |
| stage 3 | 170° C. |
| stage 4 | 170° C. |
| stage 5 | 170° C. |
| stage 6 | 200° C. |
| stage 7 | 200° C. |
| stage 8 | 200° C. |

| Reaction product (content in % by weight) | |
|---|---|
| perchloro-2,5-diaza-1,5-hexadiene | 97.6 |
| N-dichloromethyl-perchloro-2-imidazoline | 0.5 |
| N-dichloromethyl-2,4,5-trichloroimidazole | 1.8 |

EXAMPLE 7

(Discontinuous high-temperature chlorination in a stirred kettle)

A mixture of 235 kg of phosphorus oxychloride and 45 kg of N,N-dimethylaminoacetonitrile was initially introduced into a 270 liter enamel kettle with oil circulation heating, provided with a distillation column with a column head, which could be operated with an infinite or a finite reflux ratio as desired, and the hydrochloride of the nitrile was prepared by passing in 19.5 kg of hydrogen chloride. During this reaction the temperature rose to about 75° C. Chlorine was then passed in for about 12 hours until the heterogeneous reaction solution had become homogeneous. Phosphorus oxychloride was now distilled off, the temperature being increased slowly but a bottom temperature of 130° C. not being exceeded. After the distillation had ended, the reaction mixture was chlorinated for a further 10 hours at 130° C. The temperature was now raised at a rate of 10° C. per hour to 200° C., while adding further chloride, and the chlorination was continued at this temperature for a further 15 hours. If an attempt was made to chlorinate the reaction product which then resulted, to obtain higher contents of perchloro-2,5-diaza-1,5-hexadiene, side reactions took place, as can be seen from the following table:

| Content (%) | Chlorination time at 200° C. | |
|---|---|---|
| | 15 (hours) | 20 (hours) |
| Perchloro-2,5-diaza-1,5-hexadiene | 90.2 | 87.9 |
| N-Dichloromethyl-2,4,5-trichloroimidazole | 9.8 | 7.3 |
| Tetrachloropyrimidine | | 2.6 |
| 1,1,3,3-Pentachloro-2-aza-1-propene | | 1.0 |
| Unknown substances | | 1.2 |

It will be appreciated that the instant specification and examples are set forth by way of illustration and not limitation, and that various modifications and changes may be made without departing from the spirit and scope of the present invention.

What is claimed is:

1. In the preparation of perchloro-2,5-diaza-1,5-hexadiene by chlorination of N,N-dimethylaminoacetonitrile, the improvement which comprises in a first stage (a) chlorinating N,N-dimethylaminoacetonitrile or its hydrochloride at about 70° to 80° C. in a solvent selected from the group consisting of thionyl chloride, sulphuryl chloride and phosphorus oxychloride, removing the solvent by distillation under chlorinating conditions until a bottom temperature of about 120° to 160° C. is reached, and after-treating the residual reaction mixture at this temperature with chlorine, and in a second stage (b) chlorinating the resulting reaction mixture at a temperature from about 150° to 220° C.

2. A process according to claim 1, wherein stage (b) is carried out in a multi-stage bubble column cascade reactor.

3. A process according to claim 2, wherein the bubble column cascade reactor is operated with gas and liquid in counter-current.

4. A process according to claim 1, wherein the after-chlorination stage (a) is carried out at a temperature from about 110° to 150° C.

5. A process according to claim 1, wherein the solvent used in stage (a) is phosphorus oxychloride.

6. A process according to claim 1, wherein stage (b) is carried out at a temperature from about 160° to 210° C.

7. A process according to claim 1, wherein the weight ratio of the nitrile to solvent in stage (a) is about 1:1 to 1:10.

8. A process according to claim 3, wherein the solvent in stage (a) is phosphorus oxychloride, the weight ratio of nitrile to solvent is about 1:3, the after-chlorination in stage (a) is carried out at a temperature from about 120° to 140° C., and stage (b) is carried out at a temperaure from about 180° to 210° C.